US009188529B2

(12) United States Patent
Shpaisman et al.

(10) Patent No.: US 9,188,529 B2
(45) Date of Patent: Nov. 17, 2015

(54) HOLOGRAPHIC MICROREFRACTOMETER FOR DETERMINING REFRACTIVE INDEX OF A MEDIUM

(71) Applicant: New York University, New York, NY (US)

(72) Inventors: Hagay Shpaisman, Highland Park, NJ (US); Bhaskar Jyoti Krishnatreya, Astoria, NY (US); David G. Grier, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/380,286

(22) PCT Filed: Feb. 21, 2013

(86) PCT No.: PCT/US2013/027112
§ 371 (c)(1),
(2) Date: Aug. 21, 2014

(87) PCT Pub. No.: WO2013/126554
PCT Pub. Date: Aug. 29, 2013

(65) Prior Publication Data
US 2015/0062587 A1 Mar. 5, 2015

Related U.S. Application Data

(60) Provisional application No. 61/634,211, filed on Feb. 24, 2012, provisional application No. 61/604,309, filed on Feb. 28, 2012.

(51) Int. Cl.
*G01N 21/45* (2006.01)
*G01N 21/41* (2006.01)
(Continued)

(52) U.S. Cl.
CPC .......... *G01N 21/453* (2013.01); *G01N 15/1429* (2013.01); *G01N 15/1456* (2013.01);
(Continued)

(58) Field of Classification Search
CPC .................... G01N 21/453; G01N 2015/1454; G01N 21/41; G01N 21/4133; G01N 21/45; G01N 15/1429; G01N 15/1456
See application file for complete search history.

(56) References Cited

U.S. PATENT DOCUMENTS

| 5,146,086 A | 9/1992 | De et al. |
| 8,766,169 B2 * | 7/2014 | Grier et al. .................... 250/251 |

(Continued)

FOREIGN PATENT DOCUMENTS

| WO | WO2009/059008 | 5/2009 |
| WO | WO2010/101671 | 9/2010 |
| WO | WO2013/126554 | 8/2013 |

OTHER PUBLICATIONS

Lee et al., Characterizing and tracking single colloidal particles with video holographic microscopy, Optics Express, vol. 15, No. 26, pp. 18275-18282, Dec. 20, 2007.
(Continued)

*Primary Examiner* — Michael A Lyons
*Assistant Examiner* — Violeta A Prieto
(74) *Attorney, Agent, or Firm* — Foley & Larnder LLP

(57) ABSTRACT

An in-line holographic microscope is used for measurements of micrometer-scale particles and associated suspending fluid medium containing the particles. The system yields heterodyne scattering patterns that may be interpreted with Lorenz-Mie theory to obtain precise time-resolved information on the refractive index of the suspending medium for determining chemical composition, concentrations and makeup thereof. This approach can perform spatially resolved refractometry with measurements on calibrated refractive index standards and monitor chemical concentration in a microfluidic channel. Using commercially available colloidal spheres as probe particles and a standard video camera for detection yields volumetric refractive index measurements with a resolution of $2\times10^{-3}$ RIU for each probe particle in each holographic snapshot.

16 Claims, 4 Drawing Sheets

(51) Int. Cl.
*G02B 21/36* (2006.01)
*G01N 15/14* (2006.01)
*G01N 21/47* (2006.01)

(52) U.S. Cl.
CPC ............ G01N21/41 (2013.01); G01N 21/4133 (2013.01); G02B 21/361 (2013.01); *G01N 2015/1454* (2013.01); *G01N 2021/4707* (2013.01); *G01N 2201/0612* (2013.01); *G01N 2201/08* (2013.01)

(56) References Cited

U.S. PATENT DOCUMENTS

| | | | |
|---|---|---|---|
| 8,791,985 B2* | 7/2014 | Grier et al. | 348/40 |
| 2011/0043607 A1* | 2/2011 | Grier et al. | 348/40 |
| 2012/0273664 A1* | 11/2012 | Grier et al. | 250/251 |
| 2013/0278743 A1* | 10/2013 | Cheong et al. | 348/79 |
| 2014/0333935 A1* | 11/2014 | Grier et al. | 356/457 |

OTHER PUBLICATIONS

Cheong et al., "Holographic characterization of individual colloidal spheres porosities", Soft Matter, vol. 7, No. 15, pp. 6816-6819, Jun. 22, 2011.

Notification of Transmittal of The International Search Report and The Written Opinion of the International Searching Authority for PCT App. PCT/US2013/027112, dated Jun. 11, 2013, 11 pages.

Notification Concerning Transmittal of International Preliminary Report on Patentability for PCT App. PCT/US2013/027112, dated Sep. 4, 2014, 8 pages.

* cited by examiner

HOLOGRAPHIC MICROREFRACTOMETER FOR DETERMINING REFRACTIVE INDEX OF A MEDIUM

CROSS-REFERENCE TO RELATED PATENT APPLICATIONS

This application is a PCT National Phase application of PCT/US2013/027112, filed Feb. 21, 2013, which claims the benefit of U.S. Provisional Patent Application No. 61/634,211, filed Feb. 24, 2012 and U.S. Provisional Patent Application No. 61/604,309, filed Feb. 28, 2012, 2012. All applications are incorporated herein by reference in their entirety.

GOVERNMENT RIGHTS

This work was supported by the National Science Foundation through Award No. DMR-0922680 and the U.S. Government has certain rights in this invention.

BACKGROUND OF THE INVENTION

Optical probes are essential to many lab-on-a-chip systems which require precise time-resolved information on the refractive index of a fluid medium. Considerable effort, therefore, has been focused on developing techniques to measure the refractive index of picoliter samples using refractive index probes. One approach is to integrate a refractometer into the microfluidic device, with examples including instruments based on beam deflection photonic crystal resonators Fabry-Perot interferometers and other microfabricated resonators. The best of these methods and systems can achieve a resolution of $10^{-7}$ refractive index units (RIU). The principal disadvantage is the need to microfabricate the refractometer and integrate it with the microfluidic system.

Chemically synthesized colloidal spheres dispersed in the fluid medium also have been used as probes of the local refractive index through spectroscopy of their whispering gallery modes. When these modes are excited by broadband fluorescence of dye molecules or quantum dots embedded in the probe sphere itself, the local refractive index can be measured with a resolution of $2.5 \times 10^{-4}$ RIU. The necessary spectroscopic measurements, however, limit this approach to addressing one probe particle at a time. The fluid medium, moreover, must be chemically and physically compatible with the specially synthesized spheres.

SUMMARY OF THE INVENTION

In the method and system of the invention a complementary approach to microrefractometry has been developed based on holographic imaging of suspended colloidal spheres in a fluid medium. This method and system yield time resolved measurements of the refractive index, and therefore determine chemical concentrations and even composition, at multiple points simultaneously using a standard video camera as a detector, and achieves a resolution approaching $10^{-3}$ RIU. Because virtually any type of colloidal sphere can act as the probe, this technique is compatible with a wide range of chemical conditions.

Various aspects of the invention are described herein; and these and other improvements are described in greater detail hereinbelow, including the drawings described hereinafter.

DETAILED DESCRIPTION OF PREFERRED EMBODIMENTS

Figure 1A:
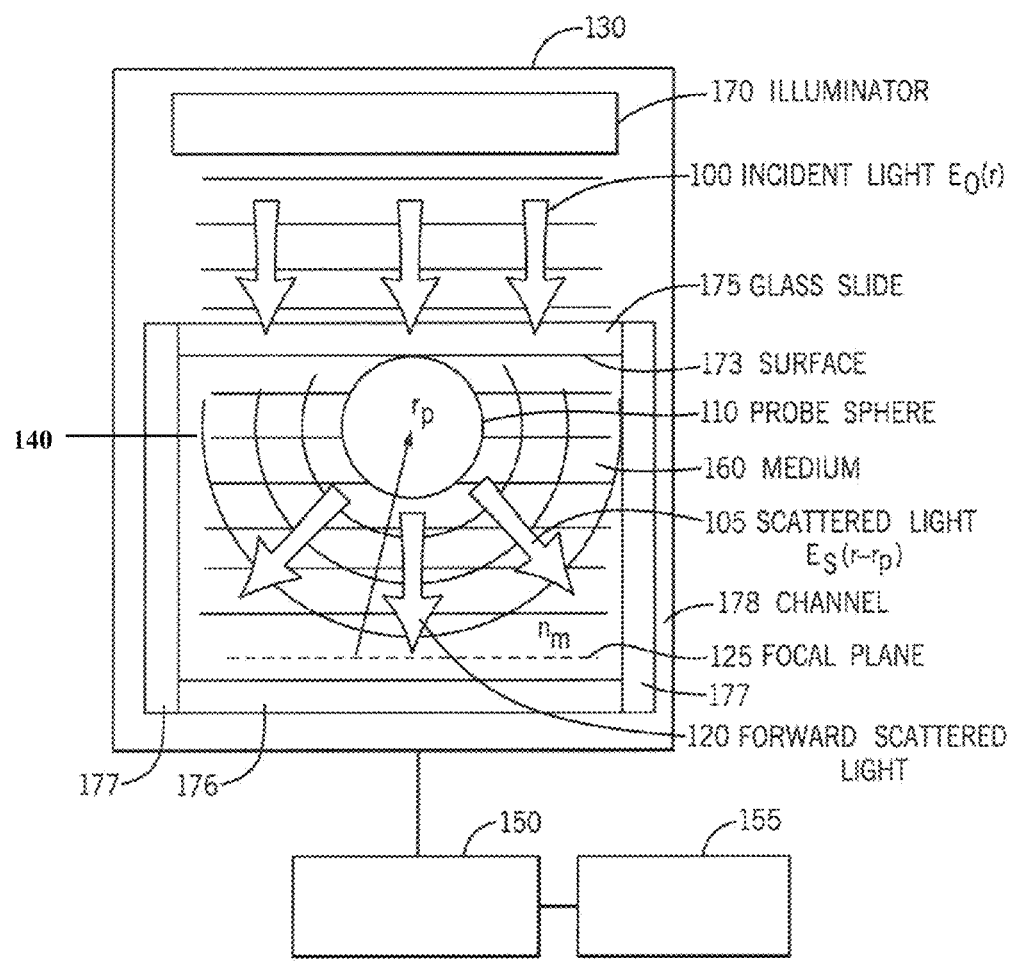
FIG. 1A shows a schematic of incident light interacting with a refractive index probe sphere in a sample medium.
Figure 1B:
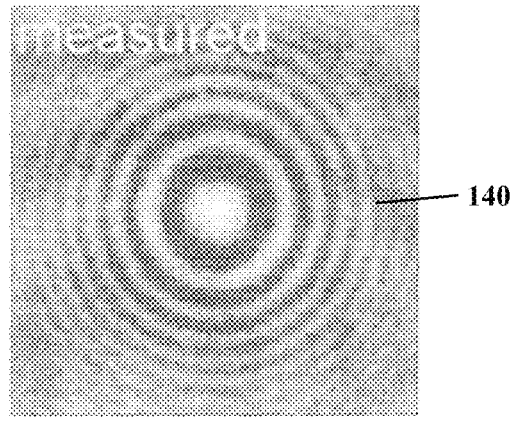
FIG. 1B shows a measured hologram arising from the light and refractive index probe and medium interaction of FIG. 1A
Figure 1C:
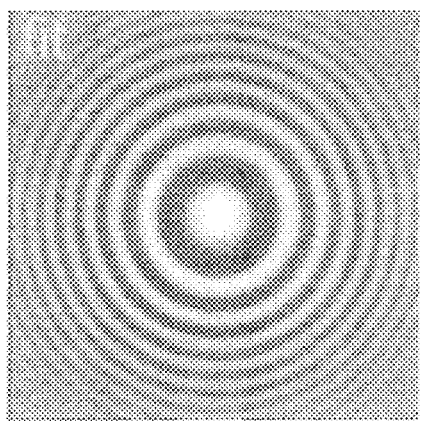
FIG. 1C shows a fitted hologram using methods of the invention.

Our method and system is based on in-line holographic video microscopy, shown schematically in FIGS. 1A-1C, in which a refractive index probe 110 (e.g., a refractive index probe sphere) is illuminated with a collimated beam of coherent light 100. The light 105 scattered by the refractive index probe 110 (embedded in medium 160) and interferes with the unscattered portion 120 of the illumination in the focal plane 125 of an otherwise conventional optical microscope 130. The interference pattern 140 is magnified and its intensity is recorded with a video camera 150. A computer/memory system 155 having a non-transitory memory and computer read/writability media for executing computer software therein can be used to analyze the intensity data using appropriate computer software in the media. Such a system as the system 155 can be e.g., entirely or part of or include other components and can include various microprocessors RAM, ROM and drives or other external media and memory devices or be in the cloud. The system 155 can for example, include a display and/or input device and can be implemented by a network or "in the cloud" or in other remote linked systems and devices. Further details of the system 155 will be provided hereinafter. The system 155 can further include other output devices for viewing and printing information for analysis and further data processing. Each digitized image is a hologram arising from the light incident on the refractive index probe 110 in the media and provides comprehensive information on three-dimensional structure and composition of the medium 160. Holographic snapshots can be interpreted with predictions of a selected theory of light scattering, such as the Lorenz-Mie theory of light scattering, to track colloidal particles with nanometer resolution in three dimensions over a range extending to hundreds of micrometers. The same analysis also yields detailed information on individual particles' sizes and refractive indexes, which can be further interpreted to detect molecular-scale coatings and to measure individual particles' porosities. Here, we use data from holographic microscopy not to track and characterize the individual colloidal particles, but rather to characterize the chemical makeup of the surrounding medium 160.

The holographic microscope 130 preferably illuminates the refractive index probe 110 disposed in the medium 160 with the collimated beam of light 100 from an illuminator 170, such as an array of fiber-coupled diode lasers (iFlex Viper). The scattered light of the interference pattern 140 is collected with a 100× numerical aperture 1.4 oil immersion objective (Nikon, Plan Apo) and is relayed as grayscale or color data to a video camera 150 (NEC TI-324A), which records holograms at thirty frames/s. The intensity measured at position r in the focal plane 125 results from the superposition of an incident field $E_o(r)$, which we model as a plane wave linearly polarized on the $\hat{x}$ direction, and the field $E_s(r-r_p)$ scattered by a particle (the refractive index probe 110) at position $r_p$, relative to the center of the focal plane 125:

$$I(r)=|E_o(r)+E_s(r-r_p)|^2 \quad (1)$$

For spherical probe particles for the refractive index probe 110, $E_s(r)$ preferably is described by the Lorenz-Mie theory of light scattering and is parameterized by the radius $a_p$, of the refractive index probe 110 and by its refractive index $n_p(\omega)$ relative to that of the medium 160, $n_m(\omega)$. This latter dependence enables us to use holograms of colloidal spheres for the refractive index probe 110 to monitor the refractive index of the medium 160 with spatial resolution set by the scale of the measured scattering pattern and temporal resolution of the video camera's frame rate.

Measured holograms of colloidal spheres for the refractive index probe 110 are normalized by measured background images and fit to the predictions of Lorenz-Mie theory for each refractive index probe particle's position $r_p$, radius $a_p$, and relative refractive index $n_p(\omega)/n_m(\omega)$. The computer system 155 is used to perform such Lorenz-Mie analysis by executing software stored therein as described hereinbefore. The fitting procedure has been described in detail in US Patent Publication No. US2001/0043607A1 which is incorporated by reference herein in its entirety. If the refractive index of the probe particle (the refractive index probe 110) is independently calibrated, the fit yields the refractive index of the medium 160 in the vicinity of the refractive index probe 110 with time resolution set by the exposure time and frame rate of the video camera 150.

The technique is validated by analyzing holograms of 1 μm diameter colloidal silica spheres for the refractive index probe 110 (Thermo Scientific, Catalog Number 8100) dispersed in a set of ten refractive index standards (Cargille Laboratories, series AAA) with refractive indexes ranging from 1.30 to 1.39 RIU. Probe spheres for the refractive index probe 110 were attached to the upper surface 173 of a glass slide 175 of a microfluidic channel 178 as shown in FIG. 1A. The glass surface 173 of the slide 175 is initially cleaned by washing in deionized water, sonicating for 30 minutes in acetone, and oxygen plasma etching for another 30 minutes. An aqueous dispersion of spheres for the refractive index probe 110 in deionized water then is spread over the clean dry surface 173 and allowed to dry for 2 hours in a 10-100 Torr dessicator. The decorated surface 173 of the glass slide 175 is then exposed for 20 hours to a room-temperature vapor of hexamethyldisilazane (HMDS 99.9%, Aldrich) in a closed glass container. This coating permanently affixes the spheres of the refractive index probe 110 to the surface 173 of the glass slide 175 and also minimizes fluid imbibation that otherwise might have changed the spheres' effective refractive indexes. The other wall of a channel 178 is formed by a clean number one cover slip.

The channel 178 then was mounted on the stage of the holographic microscope 130 for measurements. A typical 80×70 μm² field of view includes 5 spheres for the refractive index probe 110 whose holographic images are sufficiently widely separated for each analysis. Each probe sphere's refractive index is calibrated by filling the channel 178 with a refractive index standard (nominally $n_m$=1.3300 at 589.3 nm, corrected to $n_m$=1.3291 at 640 nm) and fitting its measured hologram as previously described. The spheres' holograms are not appreciably affected by contact with upper surface 173 (the surface 173 is directly above the sphere in FIG. 1A, and the sphere is shown touching the surface 173. The surface 173 is thus indicated by a horizontal line), except that additional light 105/120 is projected onto the few pixels closest to the forward-scattering direction. Because these pixels' influence on the fits is smaller than the overall measurement uncertainty, no effort is made to correct for them. The calibrated probe spheres of the refractive index probe 110 then are used as probes of the refractive index and associated chemical properties and composition of other fluids of the medium 160 flowing down the channel 178.

Figure 2A:
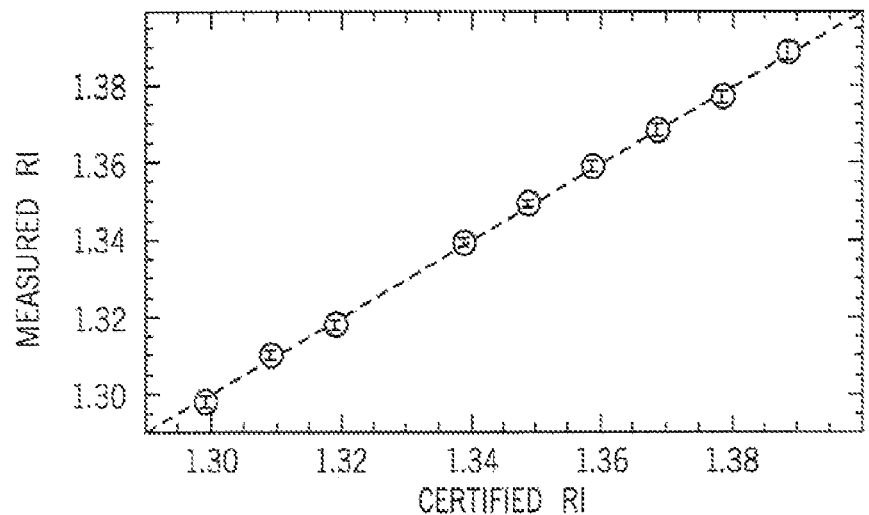
FIG. 2A shows a comparison of measured and certified values of refractive index of nine reference index standards based on calibration of a refractive index probe sphere with a tenth standard.
Figure 2B:
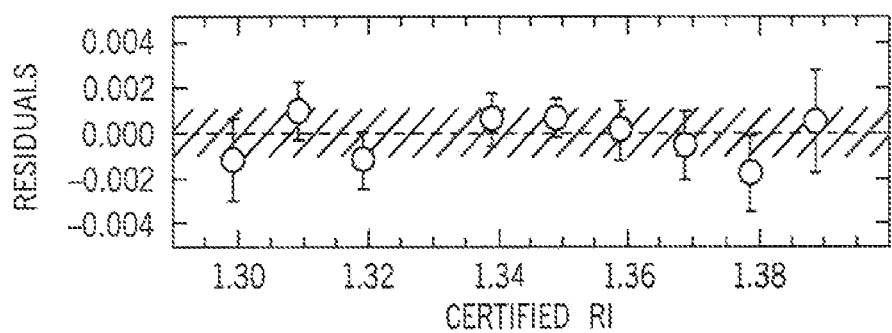
FIG. 2B shows a plot of residuals for the nine reference index standards with the cross-hatched region in the residuals plot corresponding to the estimated $10^{-3}$ RIU uncertainty in fit values for the refractive index.

The data in FIGS. 2A and 2B were obtained by filling the channel 178 with the refractive index probes 110 of certified refractive index standards (and having associated chemical characteristics and composition) and fitting for the refractive index of the fluid medium 160 rather than that of the refractive index probe 110. The certified refractive indexes of the standard fluids were corrected for the 640 nm illumination following the manufacturer's instructions. Between measurements, the channel 178 and its refractive index probes 110 were thoroughly cleaned by washing three times with DI water, acetone, and methanol, and then were dried with a stream of clean dry nitrogen.

Each measurement was performed by analyzing 30 holograms of four probe spheres for the refractive index probe 110 that were recorded over 1 s. The individual fits' precision is typically $10^{-4}$ RIU. The error bars in FIG. 2 reflect the $2\times10^{-3}$ RIU range of values for Tin, obtained from the four spheres of the refractive index probe 110. We ascribe this loss of accuracy relative to the measurements' precision to optical imperfections introduced while affixing the probe spheres of the refractive index probe 110 to the surface of the glass slide 175. It is not however an inherent limitation of the method.

The same data sets were reanalyzed using the certified values of the fluids' refractive indexes as inputs, this time to confirm that the spheres' measured refractive indexes did not vary with that of the medium 160. The absence of correlation between $n_p$, and $n_m$, in this analysis confirms that the treated spheres of the refractive index probe 110 were impervious.

Figure 3:
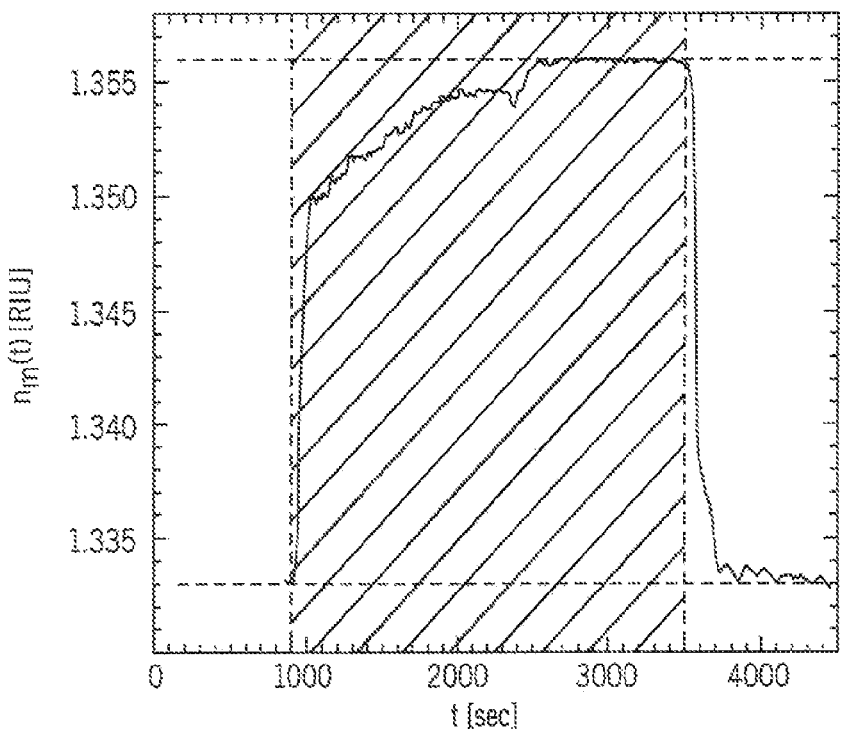
FIG. 3 shows a plot of time-resolved measurements of refractive index of an aqueous sucrose solution in a microfluidic channel with the cross-hatched region indicating the period during which sucrose solution is flowing into the channel.

The data in FIG. 3 demonstrate the use of holographic microrefractometry for monitoring changes in the chemical and physical character of the fluid medium 160 within a microfluidic channel 178. Only a portion of the channel 178 is indicated in FIG. 1A. The channel 178 consists of an upper glass surface 173 to which the sphere is attached, a lower glass surface 176, and side walls 177 that consist of the glue that holds the channel 178 together. A stream of deionized water flowing at 0.5 μL/s is abruptly returned to pure water. During this process, the fluid's measured refractive index increases from $n_m$=1.333±0.002, to $n_m$=1.356+0.002 as sugar solution suffuses the channel 178, and returns to its baseline value once the sucrose is washed out. The $2\times10^{-3}$ RIU accuracy for refractive index in this measurement corresponds to a 30 nM resolution for sucrose concentration.

An estimate suggests that the entire volume of the channel 178 would be replaced every 2 s, and that sugar solution would entirely fill the channel 178 in a matter of seconds. The actual half-time for replacing the water with sucrose extends to several minutes, presumably because reservoirs of fluid form in the tubing leading to the microfluidic channel 178.

In addition to using randomly deposited spheres as the refractive index probes 110, we also have used holographic optical traps to attach the refractive index probes 110 to selected locations within the microfluidic channels 178. In this case, the refractive index probes 110 were dispersed in a 200 mM solution of $Na_2SO_4$. Pressing one of the refractive index probes 110 against a surface of the glass slide 175 for roughly 10 s suffices to fix it in place. This provides a simple means to position the refractive index probes 110 at specific locations.

These measurements demonstrate that colloidal spheres of the refractive index probes 110 can be used as effective probes of the local refractive index and associated chemical and physical properties of the fluid medium 160. Requiring only optical access for imaging with collimated laser illumination, holographic refractometry is easily integrated with existing lab-on-a-chip systems.

Figure 4:
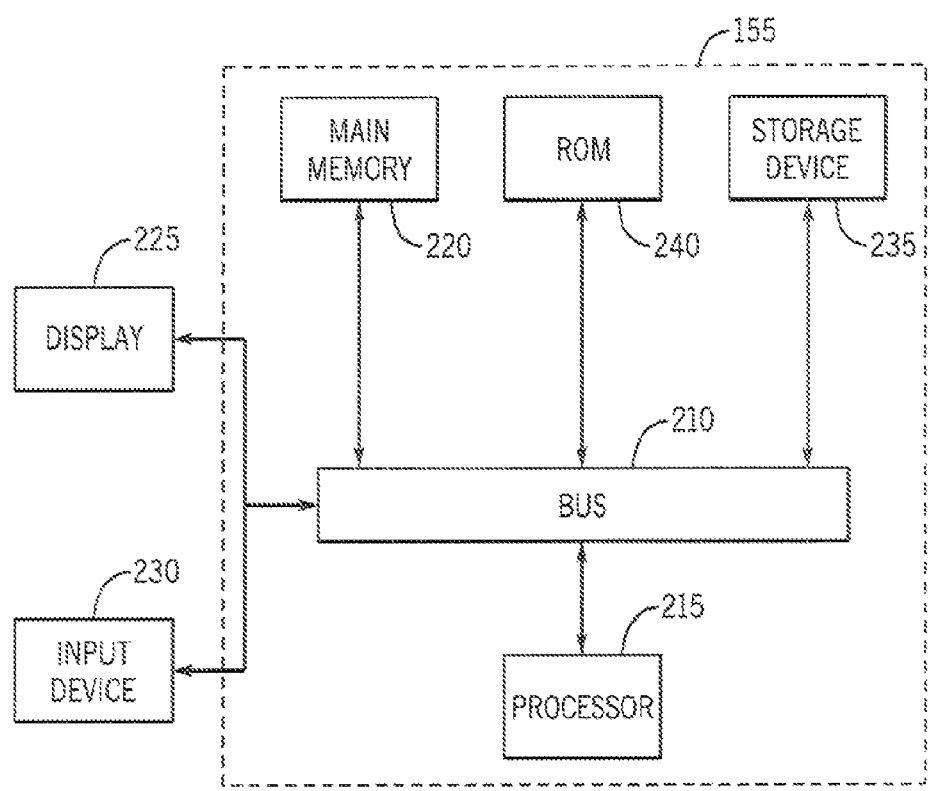
FIG. 4 shows a computer system used to perform data analysis for a method of the invention.

FIG. 4 is a detailed block diagram of the computer system 155 in accordance with an illustrative implementation. The computer system 155 or can be used to implement a device that includes a processor 215 and the display 205, etc. The computer system 155 includes a bus 210 or other communication component for communicating information and a processor 215 or processing circuit coupled to the bus 210 for processing information. The computing system 155 can also include one or more of the processors 215 or processing circuits coupled to the bus 210 for processing information. The computer system 155 also includes main memory 220, such as a random access memory (RAM) or other dynamic storage device, coupled to the bus 210 for storing information, and instructions to be executed by the processor 215. Main memory 220 can also be used for storing position information, temporary variables, or other intermediate information during execution of instructions by the processor 215. The computer system 155 may further include a read only memory (ROM) 240 or other static storage device coupled to the bus 210 for storing static information and instructions for the processor 215. A storage device 235, such as a solid state device, magnetic disk or optical disk, is coupled to the bus 210 for persistently storing information and instructions.

The computing system 155 may be coupled via the bus 210 to a display 225, such as a liquid crystal display, or active matrix display, for displaying information to a user. An input device 230, such as a keyboard including alphanumeric and other keys, may be coupled to the bus 210 for communicating information and command selections to the processor 215. In another implementation, the input device 230 has a touch screen display 225. The input device 230 can include a cursor control, such as a mouse, a trackball, or cursor direction keys, for communicating direction information and command selections to the processor 215 and for controlling cursor movement on the display 225.

According to various implementations, the processes described herein can be implemented by the computing system 155 in response to the processor 215 executing an arrangement of instructions contained in main memory 220. Such instructions can be read into main memory 220 from another computer-readable medium, such as the storage device 235. Execution of the arrangement of instructions contained in main memory 220 causes the computing system 155 to perform the illustrative processes described herein. One or more processors in a multi-processing arrangement may also be employed to execute the instructions contained in main memory 220. In alternative implementations, hardwired circuitry may be used in place of or in combination with software instructions to effect illustrative implementations. Thus, implementations are not limited to any specific combination of hardware circuitry and software.

Although an example computing system has been described in FIG. 4, implementations of the observer matter and the functional operations described in this specification can be implemented in other types of digital electronic circuitry, or in computer software, firmware, or hardware, including the structures disclosed in this specification and their structural equivalents, or in combinations of one or more of them.

Implementations of the observer matter and the operations described in this specification can be implemented in digital electronic circuitry, or in computer software, firmware, or hardware, including the structures disclosed in this specification and their structural equivalents, or in combinations of one or more of them. The observer matter described in this specification can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described in this specification can be performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the observer matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

Thus, particular implementations of the observer matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

The invention claimed is:

1. A method for determining refractive index at a plurality of points in a medium, comprising the steps of:
    providing a source of light for generating a collimated beam of coherent light;
    providing an optical microscope having a focal plane;
    providing a fluid medium whose refractive index is to be determined;
    providing a refractive index probe comprised of at least one probe particle disposed in the medium;
    inputting the coherent light to the optical microscope and illuminating the at least one probe particle disposed in the medium;
    forming an interference pattern in the focal plane from light scattered by the at least one probe particle and an unscattered portion of the collimated beam;
    recording the interference pattern; and
    analyzing the interference pattern and fitting the pattern to obtain the refractive index of the medium in the focal plane of the refractive index probe in the medium.

2. The method as defined in claim 1 wherein interference pattern intensity is described by $$I(r)=|E_0(r)[=]\pm E_s(r-r_p)|^2,$$

where the at least one probe particle is at a position $r_p$ relative to a center of the focal plane, $E_0(r)$ is the incident field, modeled as a plane wave linearly polarized on the [circumflex over (x)] direction, $E_s(r-r_p)$ is the field scattered by a particle at position $r_p$, relative to the center of the focal plane, and $I(r)$ is measured at position r in the focal plane.

3. The method as defined in claim 1 wherein the step of analyzing comprises applying a Lorenz-Mie methodology.

4. The method as defined in claim 3 wherein a computer system executes computer software characteristic of the Lorenz-Mie methodology.

5. The method as defined in claim 1 wherein the refractive index probe comprises a plurality of particles.

6. The method as defined in claim 5 wherein the refractive index is determined at each location of the plurality of particles.

7. The method as defined in claim 5 wherein the plurality of particles comprise spherical particles.

8. The method as defined in claim 3 wherein particle position, particle radius and relative index of refraction are determined by fitting the Lorenz-Mie methodology to the interference pattern.

9. The method as defined in claim 1 wherein refractive index of the refractive index probe is independently calibrated, thereby enabling determination of the refractive index of the refractive index probe of the at least one particle.

10. A system for determining refractive index at a plurality of points in a medium, comprising:
    a source of light for generating a collimated beam of coherent light;
    an optical microscope having a focal plane;
    a fluid medium whose refractive index is to be determined;
    a refractive index probe comprised of at least one particle disposed in the medium wherein the coherent light is input and interacts with the at least one particle to provide an interference pattern in the focal plane;
    a video camera in communication with the optical microscope and configured to record the interference pattern; and
    a computer in communication with the video camera configured to receive the interference pattern and analyze the interference pattern and fitting the pattern to predict particle position, particle radius and relative refractive index to obtain refractive index of the medium in the focal plane of the refractive index probe in the medium.

11. The system as defined in claim 10 wherein interference pattern intensity is described by $$I(r)=|E_0(r)[=]\pm E_s(r-r_p)|^2,$$

where the refractive index probe is at a position $r_p$ relative to a center of the focal plane, $E_0(r)$ is the incident field modeled as a plane wave linearly polarized on the [circumflex over (x)] direction $E_s(r-r_p)$ is the field scattered by a particle at position $r_p$, relative to the center of the focal plane, and $I(r)$ is measured at position r in the focal plane.

12. The system as defined in claim 10 further including an executable program in the computer for applying a Lorenz-Mie methodology to the interference pattern.

13. The system as defined in claim 10 wherein the refractive index probe comprises a plurality of particles.

14. The system as defined in claim 12 wherein the computer and the executable program refractive index of the refractive index probe is independently calibrated, thereby enabling determination of the refractive index of the at least one particle.

15. A non-transitory computer-readable medium having instructions stored thereon, the instructions comprising the steps of,
    receiving data pertaining to an optical interference pattern of at least one refractive index probe disposed in a medium; and
    fitting the interference pattern to obtain the refractive index of the medium in the focal plane of the refractive index probe in the medium wherein the interference pattern is formed in the focal plane from light scattered by the refractive index and an unscattered portion of a collimated beam, thereby providing data for obtaining the refractive index of the medium.

16. The computer-readable medium of claim 15 wherein the instructions further include analyzing the refractive index of the medium to determine chemical concentration and composition.

* * * * *